(12) United States Patent
Hatahori et al.

(10) Patent No.: US 10,429,172 B2
(45) Date of Patent: Oct. 1, 2019

(54) DEFECT DETECTION METHOD AND DEFECT DETECTION DEVICE

(71) Applicant: SHIMADZU CORPORATION, Kyoto-shi, Kyoto (JP)

(72) Inventors: Takahide Hatahori, Kyoto (JP); Yuya Nagata, Kyoto (JP); Kenji Takubo, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 16/004,966

(22) Filed: Jun. 11, 2018

(65) Prior Publication Data
US 2018/0356205 A1 Dec. 13, 2018

(30) Foreign Application Priority Data
Jun. 12, 2017 (JP) .................... 2017-115398

(51) Int. Cl.
  *G01N 21/45* (2006.01)
  *G01B 9/02* (2006.01)
  *G01N 29/00* (2006.01)

(52) U.S. Cl.
  CPC ..... *G01B 9/02095* (2013.01); *G01B 9/02098* (2013.01); *G01N 21/45* (2013.01); *G01N 29/00* (2013.01); *G01N 2021/458* (2013.01)

(58) Field of Classification Search
  CPC .. G01N 29/2418; G01N 29/043; G01N 21/45; G01N 21/88; G01B 9/02098; G01B 9/2095
  See application file for complete search history.

(56) References Cited

U.S. PATENT DOCUMENTS

| 4,567,769 A * | 2/1986 | Barkhoudarian | G01H 9/006 374/5 |
| 4,581,939 A | 4/1986 | Takahashi | |

(Continued)

FOREIGN PATENT DOCUMENTS

| CN | 107462581 A | 12/2017 |
| JP | 2004-101189 A | 4/2004 |
| JP | 2017219318 A | 12/2017 |

OTHER PUBLICATIONS

Communication dated Jul. 31, 2018 from the United States Patent and Trademark Office in counterpart U.S. Appl. No. 15/611,254.
(Continued)

*Primary Examiner* — Maurice C Smith
(74) *Attorney, Agent, or Firm* — Sughrue Mion, PLLC (57) ABSTRACT

A defect detection method includes the following processes: a) stroboscopically illuminating the entire surface of an object within an examination area of the object while inducing a first elastic wave across the examination area on the object, and controlling the phase of the elastic wave and the timing of the stroboscopic illumination to collectively measure a back-and-forth displacement of each point within the examination area in at least three phases of the elastic wave; b) identifying a surface location which is the location of a defect on the examination area, based on the back-and-forth displacement of each point within the examination area in the at least three different phases; and c) injecting a second elastic wave into a region inside the surface location from a limited area including the surface location, and determining the location and/or size in the depth direction of the defect, based on a response wave.

17 Claims, 4 Drawing Sheets

(56) References Cited

U.S. PATENT DOCUMENTS

| | | | | |
|---|---|---|---|---|
| 5,439,157 A | * | 8/1995 | Geier | B23K 31/12 228/5.7 |
| 5,546,187 A | * | 8/1996 | Pepper | G01D 5/48 356/487 |
| 6,057,927 A | * | 5/2000 | Levesque | G01B 11/18 356/432 |
| 2003/0057972 A1 | | 3/2003 | Pfaff et al. | |
| 2005/0023434 A1 | * | 2/2005 | Yacoubian | G01N 29/2418 250/200 |
| 2007/0157730 A1 | * | 7/2007 | Ochiai | F22B 37/003 73/627 |
| 2008/0243441 A1 | | 10/2008 | Chen et al. | |
| 2009/0007678 A1 | * | 1/2009 | Fukutomi | G01N 29/069 73/598 |
| 2011/0284508 A1 | * | 11/2011 | Miura | B23K 31/125 219/121.64 |
| 2012/0300608 A1 | | 11/2012 | Masumura | |
| 2013/0329953 A1 | | 12/2013 | Schreier | |
| 2015/0148654 A1 | | 5/2015 | Whanwook et al. | |
| 2016/0265900 A1 | | 9/2016 | Yang et al. | |
| 2017/0176393 A1 | * | 6/2017 | O'Donnell | G01N 29/46 |
| 2017/0350690 A1 | | 12/2017 | Hatahori et al. | |

OTHER PUBLICATIONS

Toshinori Nakajima, "Vibration Analysis by Holography", Oyo-Butsuri, 1972, pp. 560-573, vol. 41, No. 6.

Yoshiaki Kanno et al., "Measurement of Quartz Crystal Resonator's Vibration by Laser Horographic Interferometer", Bulletin of the Faculty of Engineering, Hokkaido University, 1982, pp. 13-20, No. 109.

U.S. Appl. No. 15/611,254, Takahide Hatahori, filed Jun. 1, 2017.

* cited by examiner

Fig. 4A
PHASE OF VIBRATION: $\phi_0$

Fig. 4B
PHASE OF VIBRATION: $\phi_1 = \phi_0 + 2\pi/3$

Fig. 4C
PHASE OF VIBRATION: $\phi_2 = \phi_0 + 4\pi/3$

DEFECT DETECTION METHOD AND DEFECT DETECTION DEVICE

TECHNICAL FIELD

The present invention relates to a method and device for detecting a defect on and in an object, such as a concrete or steel structure.

BACKGROUND ART

As a technique for detecting a defect on and in an object, such as a concrete or steel structure, a laser ultrasonic method is commonly known. In this method, while an elastic wave is induced in an object to be examined, laser light is cast onto the object and the thereby reflected light is detected with a laser interferometer to measure the displacement of the surface of the object. If a defect is present, the displacement due to the elastic wave discontinuously changes at the location of the defect. Accordingly, the defect can be detected by measuring the distribution of the displacement. However, since the detection laser (probe laser) of the laser interferometer is a point-like beam, it is necessary to scan the entire examination area of the object to be examined. Such an operation requires a considerable amount of time.

As an improved version of this technique, a method which employs electronic speckle pattern interferometry has been proposed. In this method, while an elastic wave is induced in an object to be examined, the entire examination area of the object is illuminated with laser light to generate an interference pattern, and the surface displacement is collectively measured over the entire examination area based on the interference pattern. In Patent Literature 1, this method is applied to an examination of an object having a rough surface. The entire examination area of an object to be examined is illuminated with laser light produced by expanding a laser beam using an expander. The laser light is scattered by the rough surface, forming a light-and-dark pattern called the "speckle" due to the mutual interference of the scattered rays of light. This speckle pattern is made to interfere with reference laser light branched from the illuminating laser beam, and an interference image is taken with a CCD camera or similar device. Two such images are respectively taken before and after the occurrence of a displacement on the surface of the object due to the externally given elastic wave. The distribution of the displacement on the examination area is calculated from those two images. By such a technique, the measurement of the entire examination area can be performed at one time, and a defect on or in the object can be detected based on the measured displacements.

CITATION LIST

Patent Literature

Patent Literature 1: JP 2004-101189 A

SUMMARY OF INVENTION

Technical Problem

In Patent Literature 1, the measurement of the speckle pattern is performed at only two points before and after the induction of the elastic wave, which means that only one phase state of the elastic wave is observed. If the wavelength of the elastic wave is short as compared to the size of the examination area, there will be a region with a large amplitude of wave and a region with a small amplitude within the examination area. In such a case, measuring only one phase state causes the defect-examining capability to be uneven depending on the location within the measurement area. Therefore, the defect detection device in Patent Literature 1 has a low level of defect detection accuracy.

An object under examination must be immediately repaired if it has a considerably deep defect. On the other hand, if its depth is comparatively small, it may be permissible to take the measure of monitoring the change of the defect by regular examinations rather than the immediate repair. To this end, it is necessary to determine the depth of the defect. In Patent Literature 1, the relationship among the magnitude of the surface displacement at the defect portion, length of the defect on the surface of the object, and depth of the defect is determined beforehand by a preliminary experiment or numerical calculation, based on the knowledge that those quantities have a specific relationship determined by the material and shape of the object. By using this relationship, the depth of the defect is determined from the magnitude of the displacement and the length of the defect obtained through the examination. However, this method requires the aforementioned relationship to be determined beforehand for each object made of a different material or having a different shape. Accordingly, it is impossible to easily determine the depth of the defect.

The problem to be solved by the present invention is to provide a defect detection method and defect detection device capable of quickly and accurately detecting a defect from a large examination area as well as easily measuring the depth of the defect.

Solution to Problem

The defect detection method according to the present invention developed for solving the previously described problem includes:

a) a collective displacement measurement process including: performing stroboscopic illumination on the entire surface of an object to be examined within an examination area of the object while inducing a first elastic wave across the entire examination area on the object; and controlling the phase of the elastic wave and the timing of the stroboscopic illumination to collectively measure a displacement in a back-and-forth direction of each point within the examination area in at least three mutually different phases of the elastic wave;

b) a defect location identification process including: identifying a surface location which is the location of a defect on the surface of the examination area, based on the displacement in the back-and-forth direction of each point within the examination area in the at least three different phases; and c) a depth direction information acquisition process including: injecting a second elastic wave into a region inside the surface location from a limited area on the surface including the surface location identified in the defect location identification process by a vibrator; and determining the location and/or size in the depth direction of the defect, based on a response wave of the second elastic wave.

In the collective displacement measurement process, the displacement in the back-and-forth direction (off-plane direction) of each point within the examination area on the surface of an object to be examined is collectively measured in at least three mutually different phases of an elastic wave induced in the object. Based on the collective measurement of the displacement, the surface location of a defect can be identified over the entire examination area in the defect location identification process. In this process, the entire vibrational state of the elastic wave can be reproduced at any location within the measurement area regardless of the wavelength of the elastic wave (relative to the size of the measurement area), and no unevenness in the defect-examining capability depending on the location within the measurement area occurs. Accordingly, the defect location can be identified with a high level of accuracy in the defect location identification process.

In the depth direction information acquisition process, a second elastic wave is injected into a region inside the surface location from a transducer in contact with the object within a limited area on the surface including the surface location identified in the defect location identification process, i.e. an area which is within the examination area and is more limited than the examination area, and a response wave of this second elastic wave is detected. The area which the transducer is made to come in contact with may or may not include the surface location. In the former case, the second elastic wave should be injected in the depth direction of the object to be examined. In the latter case, the wave should be obliquely injected to the surface location (the likely location of a defect). The response wave of the second elastic wave includes a wave reflected by the defect, a wave diffracted at the defect, a wave transmitted through the defect, or other forms of wave. Accordingly, it is possible to determine the location and/or size in the depth direction of the defect, based on the detected response wave. The transducer may be configured to come in contact with the object at a single point within the limited area, or to come in contact with the object at two or more points to inject the second elastic wave through each of those points. As in the case of using a high-power speaker, if the vibration can be transmitted to the object in a contactless form, it is unnecessary to make the transducer be in contact with the object.

As described to this point, with the defect detection method according to the present invention, it is possible to achieve both the quick identification of the location of a defect from a large examination area in the collective displacement measurement process and the defect location identification process, and the acquisition of information in the depth direction of the defect by a measurement performed on the limited area in the depth direction information acquisition process.

The amount of energy of the elastic wave induced in the object to be examined is proportional to the square of the frequency and the square of the amplitude. In the defect location identification process, the larger the amplitude of the first elastic wave is, the easier the measurement of the displacement in the back-and-forth direction of each point becomes. Accordingly, provided that the amount of energy is the same, the first elastic wave may preferably have a low frequency. On the other hand, in the depth direction information acquisition process, using a second elastic wave having a high frequency is preferable, since it increases the acceleration of the vibration and thereby causes a greater amount of stress, which makes it easier to detect the response wave. Furthermore, the use of a high frequency shortens the wavelength in the object and facilitates the detection of the response wave from a small defect. Accordingly, in the defect detection method according to the present invention, the second elastic wave may preferably have a higher frequency than the first elastic wave.

In the defect detection method according to the present invention, two or three of the operations of inducing the first elastic wave, injecting the second elastic wave and detecting the response wave can be performed with a common transducer. In the case where a common transducer is used for the detection of the response wave and the induction of the first elastic wave and/or injection of the second elastic wave, the transducer at the time of detection of the response wave functions as a sensor which detects vibrations by converting mechanical vibrations into electric signals. It is also possible to perform both the induction of the first elastic wave and the injection of the second elastic wave with a common oscillation circuit. In any case, the cost of the defect detection can be reduced since two or more functions can be realized with a common device.

Speckle-shearing interferometry can be applied in the collective displacement measurement process and the defect location identification process. In the speckle-shearing interferometry, the examination area is entirely illuminated with laser light, and rays of light reflected from two points whose positions are displaced in the in-plane direction of the examination area are made to interfere with each other. By determining the phase of the interfering light, the relative displacement (in the back-and-forth direction) of the two points is detected. A method which can be used for determining the phase of the interfering light is the phase shift method in which the phase of the light from two points are changed to at least three different states. Specifically, the light from one of the two points is passed through a phase shifter, and the amount of shift by the phase shifter is set to at least three different values. It is also possible to pass the rays of light from both points through a phase shifter and thereby change the phases of the two rays of light relative to each other. In the speckle-shearing interferometry, the two rays of light used for measuring the displacement of a specific point travel through almost the same optical path. This reduces the influence of an environmental disturbance which occurs in the case where measurement light and reference light travel through different environments.

The defect detection device according to the present invention includes:

a) a first elastic wave inducer for inducing a first elastic wave in an object to be examined;

b) an illuminator for performing stroboscopic illumination on an examination area on the surface of the object to be examined;

c) a displacement measurement section for controlling the phase of the first elastic wave and the timing of the stroboscopic illumination to collectively measure a displacement in a back-and-forth direction of each point within the examination area in at least three mutually different phases of the first elastic wave;

d) a second elastic wave injector, for injecting a second elastic wave into the inside of the object to be examined;

e) a response wave detector for detecting a response wave of the second elastic wave; and f) a depth direction information acquirer for determining the location and/or size in the depth direction of the defect, based on the response wave.

Advantageous Effects of the Invention

With the defect detection method and defect detection device according to the present invention, it is possible to quickly detect a defect from a large examination area as well as obtain information in the depth direction of the defect.

DESCRIPTION OF EMBODIMENTS

An embodiment of the defect detection method and defect detection device according to the present invention is hereinafter described using FIGS. 1-6.

(1) Configuration of Defect Detection Device in Present Embodiment

Figure 1:
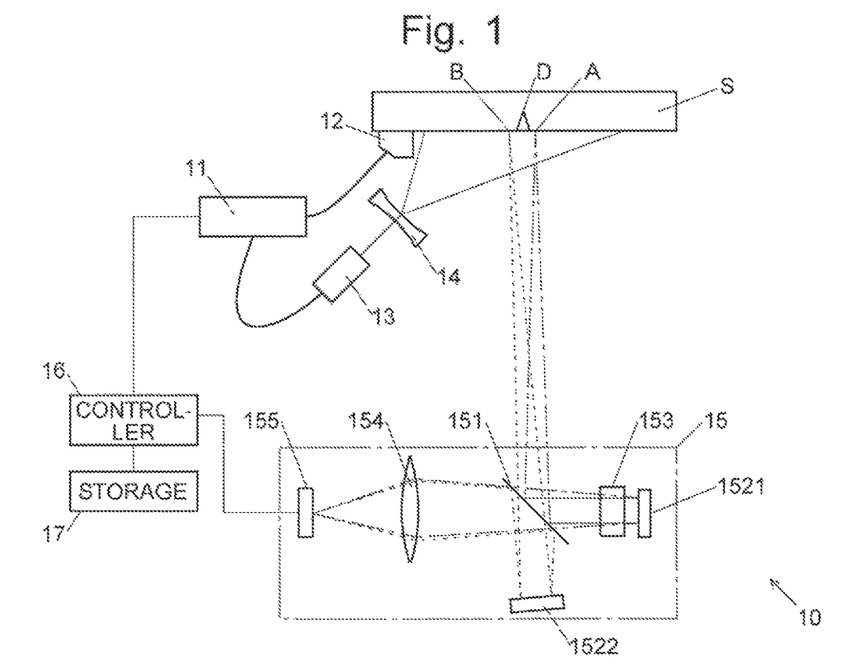
FIG. 1 is a schematic configuration diagram showing one embodiment of the defect detection device according to the present invention.

FIG. 1 is a schematic configuration diagram of a defect detection device 10 in the present embodiment. This defect detection device 10 includes a signal transmitter-receiver 11, vibrator-and-sensor (transducer) 12, pulsed laser source 13, illuminating light lens 14, speckle-shearing interferometer 15, controller 16, and storage unit 17.

The signal transmitter-receiver 11 is connected to the vibrator-and-sensor 12 via a cable. It generates an AC electric signal and transmits the signal to the vibrator-and-sensor 12. It also receives an AC electric signal generated by the vibrator-and-sensor 12, as will be described later.

When in use, the vibrator-and-sensor 12 is made to be in contact with the surface of an object S to be examined. Its contact position on the surface can be changed. The vibrator-and-sensor 12 includes a vibrating part made of a piezoelectric material. The vibrating part receives AC electric signals from the signal transmitter-receiver 11, converts those signals into mechanical vibrations (i.e. this corresponds to the function of the oscillation circuit mentioned earlier), and gives the mechanical vibrations to the object S. An elastic wave is thereby induced in the object S. In the present embodiment, both the first elastic wave and the second elastic wave are generated by the signal transmitter-receiver 11 and the vibrator-and-sensor 12. Accordingly, the signal transmitter-receiver 11 and the vibrator-and-sensor 12 function as both the first elastic wave inducer and the second elastic wave injector mentioned earlier.

The AC electric signal which the signal transmitter-receiver 11 transmits to the vibrator-and-sensor 12 has a variable frequency. When the signal transmitter-receiver 11 functions as a portion of the first elastic wave inducer, the frequency is set at a value equal to or lower than 1 MHz. When the signal transmitter-receiver 11 functions as a portion of the second elastic wave injector, the frequency is set at a value within a range of 1-10 MHz. Generating the second elastic wave at a higher frequency than the first elastic wave produces the following effects: Firstly, this allows the first elastic wave induced in the object S to have a larger amplitude than in the case of using the same frequency as the second elastic wave, making it easier to detect the displacement in the back-and-forth direction of each point within the examination area. Secondly, the second elastic wave generates the vibration with a higher level of acceleration and thereby causes a greater amount of stress than in the case of using the same frequency as the first elastic wave, making it easier to detect the response wave. Furthermore, the shortened wavelength of the second elastic wave in the object facilitates the detection of the response wave from a small defect, making it possible to obtain more accurate information in the depth direction.

When a mechanical vibration occurs in the object S, the vibrating part in the vibrator-and-sensor 12 vibrates, thereby producing an AC electric signal. Based on the AC electric signal generated in this manner, the mechanical vibration of the object S can be detected. With this function of detecting the mechanical vibration, the signal transmitter-receiver 11 and the vibrator-and-sensor 12 also function as the response wave detector mentioned earlier.

Figure 2:
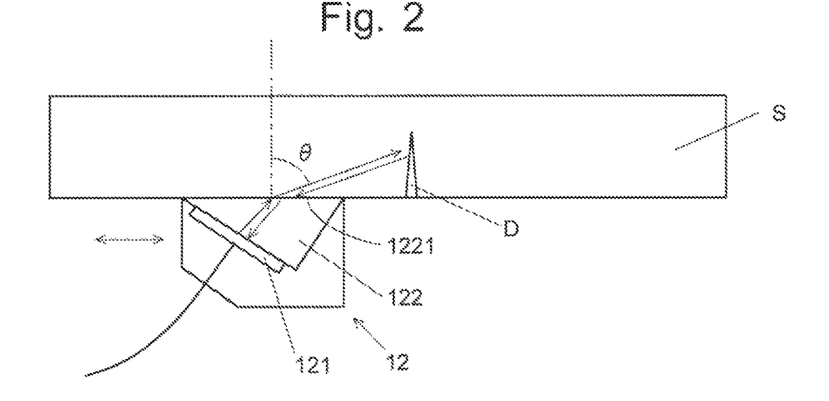
FIG. 2 is a schematic diagram showing an angle probe which is a vibrator-and-sensor used in the defect detection device in the present embodiment.

In the present embodiment, an angle probe as shown in FIG. 2 is used as the vibrator-and-sensor 12. The angle probe includes: a vibrating part 121 made of a plate-shaped piezoelectric material; and a contact part 122 which is in contact with the vibrating part 121 and has a contact surface 1221 to be in contact with an object S to be examined. The plate surface of the vibrating part 121 is not parallel to the contact surface 1221 of the contact part 122. By such a configuration, when the vibrating part 121 is driven to vibrate, an ultrasonic wave is injected from the contact surface 1221 into the object S. The higher the frequency of the ultrasonic wave is, the more directional the wave becomes. Such a highly directional ultrasonic wave having a high frequency follows a path perpendicular to the plate surface of the vibrating part 121 and obliquely enters the object S at an angle of incidence to the normal to the contact surface 1221. After being refracted at the surface of the object S, the ultrasonic wave propagates through the object S. By comparison, if the ultrasonic wave has a lower frequency, the wave becomes less directional and propagates with a more isotropic distribution from the vibrator-and-sensor 12 through the object S.

As shown in FIG. 1, the signal transmitter-receiver 11 is also connected to the pulsed laser source 13 via another cable, which is different from the one connected to the vibrator-and-sensor 12, to send a pulsed electric signal (pulse signal) to the pulsed laser source 13 at a timing when the AC electric signal mentioned earlier is at a predetermined phase. This predetermined phase and the thereby determined timing are changed during the collective displacement measurement process, as will be described later.

The pulsed laser source 13 is a light source which produces pulsed laser light upon receiving the pulse signal from the signal transmitter-receiver 11. The illuminating light lens 14, which consists of a concave lens, is placed between the pulsed laser source 13 and the object S. The illuminating light lens 14 has the function of expanding the pulsed laser light from the pulsed laser source 13 to a size that covers the entire examination area on the surface of the object S. The pulsed laser source 13 and the illuminating light lens 14 stroboscopically illuminate the examination area on the surface of the object S at the aforementioned timing. Accordingly, these devices correspond to the illuminator mentioned earlier.

The speckle-shearing interferometer 15 corresponds to the displacement measurement section mentioned earlier. It includes a beam splitter 151, first reflector 1521, second reflector 1522, phase shifter 153, condensing lens 154, and image sensor 155. The beam splitter 151 is a half mirror arranged in a manner to receive the illuminating light reflected by the examination area on the surface of the object S. The first reflector 1521 is located on an optical path of the illuminating light reflected by the beam splitter 151. The second reflector 1522 is located on an optical path of the illuminating light passing through the beam splitter 151. The phase shifter 153, which is located between the beam splitter 151 and the first reflector 1521, changes (shifts) the phase of the light which passes through the phase shifter 153. The image sensor 155 is located on an optical path of two rays of illuminating light; one ray of light is initially reflected by the beam splitter 151 and subsequently by the first reflector 1521, to eventually pass through the beam splitter 151 into the aforementioned optical path, while the other ray of light initially passes through the beam splitter 151 and is subsequently reflected by the second reflector 1522, to be eventually reflected by the beam splitter 151 into the same optical path. The condensing lens 154 is located between the beam splitter 151 and the image sensor 155.

The first reflector 1521 is arranged so that its reflecting surface is at an angle of 45° to that of the beam splitter 151, whereas the second reflector 1522 is arranged so that its reflecting surface is slightly tilted from 45° to the reflecting surface of the beam splitter 151. Such an arrangement of the first and second reflectors 1521 and 1522 produces two rays of illuminating light falling onto the same position on the image sensor 155 and interfering with each other, with one ray of light being reflected at point A on the surface of the object S and the first reflector 1521 (as indicated by long dashed short dashed lines in FIG. 1) and the other ray of light being reflected at point B slightly displaced from point A on the object surface and the second reflector 1522 (as indicated by dashed lines in FIG. 1). The image sensor 155 has a large number of detector elements. Each detector element detects light originating from a different point (point A mentioned earlier) among the large number of points on the surface of the object S and falling onto the image sensor 155 via the first reflector 1521 and the phase shifter 153. Similarly, as for point B, each detector element detects light originating from a different one of the large number of points and falling onto the image sensor 155 via the second reflector 1522.

The controller 16 controls the signal transmitter-receiver 11 and performs data processing based on the detection signal obtained from each detector element of the image sensor 155 and the AC electric signal obtained from the vibrator-and-sensor 12 via the signal transmitter-receiver 11. The storage section 17 stores the detection signal and AC electric signal, as well as the data before and after the processing by the controller 16.

Figure 3:
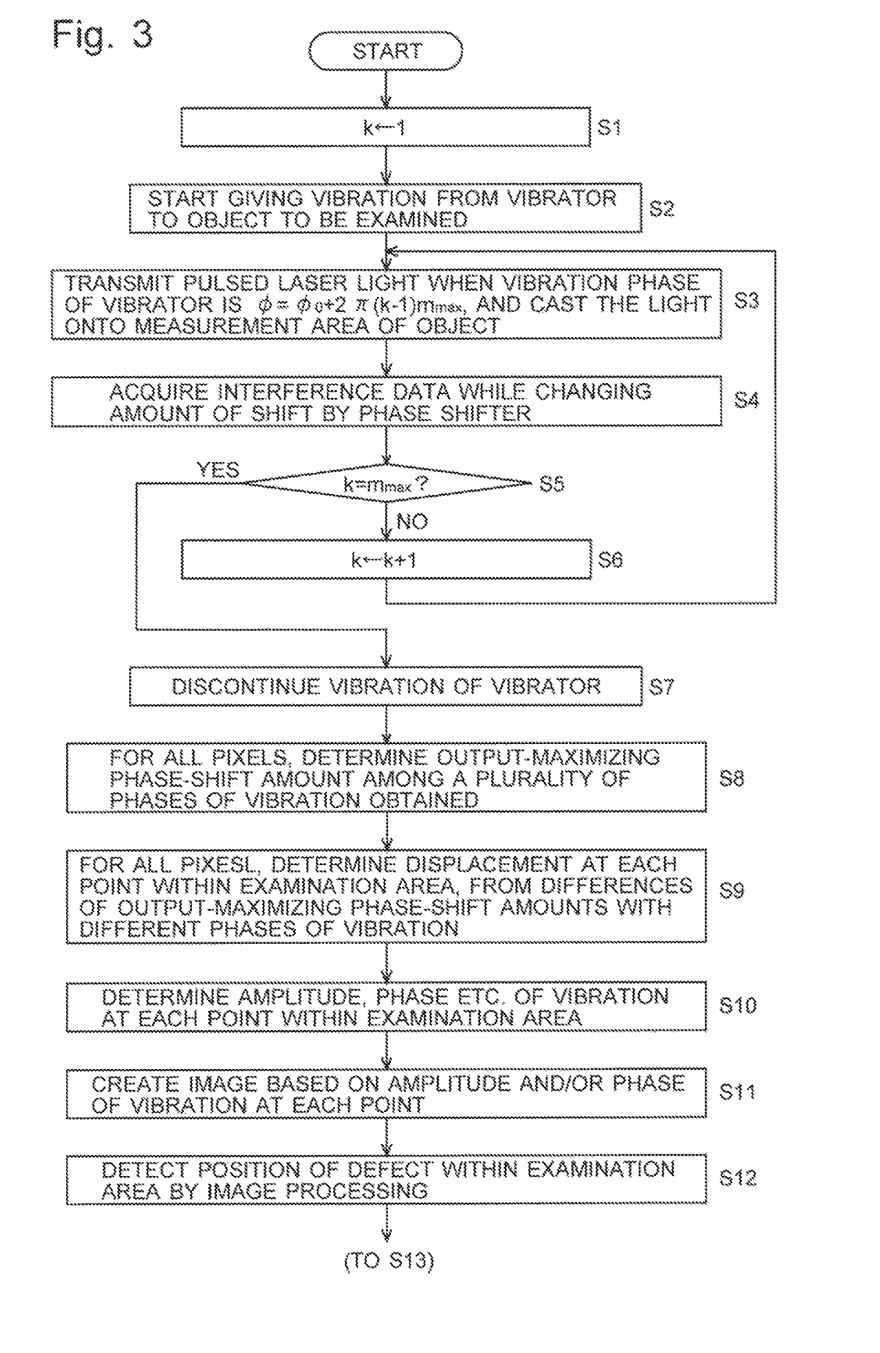
FIG. 3 is a flowchart showing the collective displacement measurement process and the defect location identification process in one embodiment of the defect detection method according to the present invention.
Figure 5:
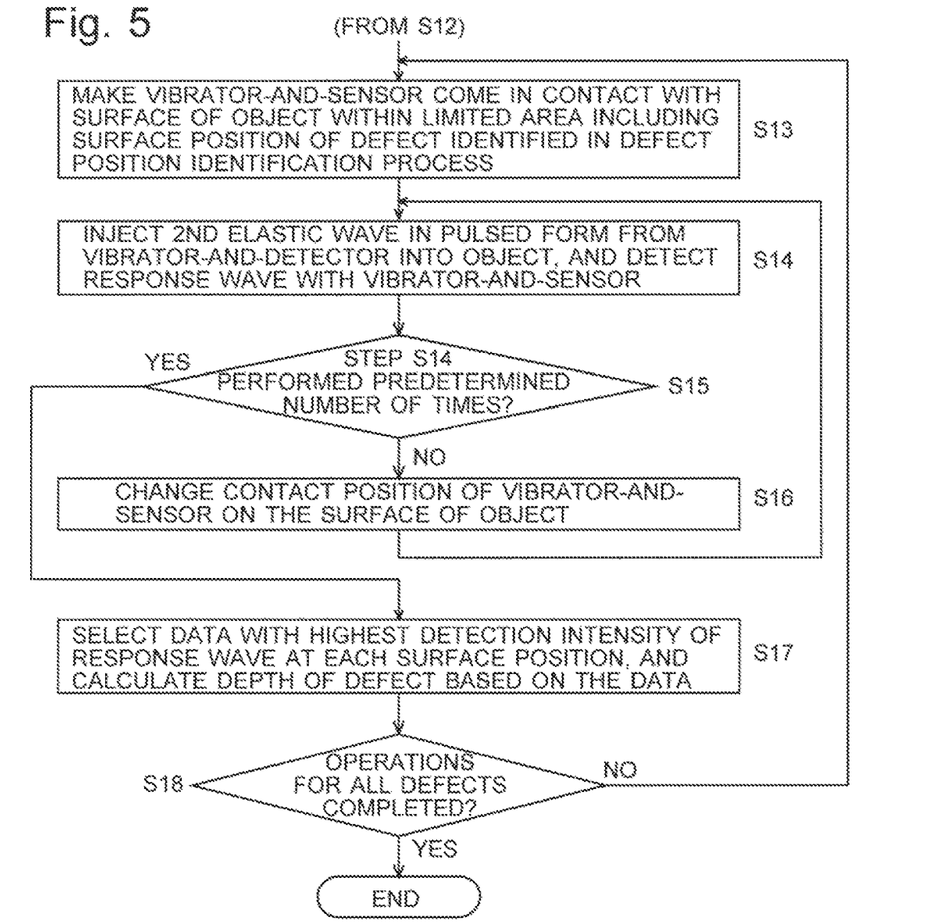
FIG. 5 is a flowchart showing the depth direction information acquisition process in the defect detection method in the present embodiment.

(2) Operation of Defect Detection Device in Present Embodiment, and Embodiment of Defect Detection Method According to Present Invention An operation of the defect detection device 10 in the present embodiment, and one embodiment of the defect detection method according to the present invention, are hereinafter described using FIGS. 3-6. FIGS. 3 and 5 are flowcharts showing the defect detection method in the present embodiment, where FIG. 3 shows the collective displacement measurement process and the defect location identification process, while FIG. 5 shows the depth direction information acquisition process (2-1) Collective Displacement Measurement Process In the present embodiment, a measurement is performed three or more times with different phases of the vibration of the vibrator-and-sensor 12 as the collective displacement measurement. The number of measurements performed with different phases of the vibration is hereinafter denoted by "$m_{max}$". In the collective displacement measurement process, the signal transmitter-receiver 11 and the vibrator-and-sensor 12 are simply used as the signal transmitter and the vibrator, respectively. Accordingly, these devices are respectively referred to as the "signal transmitter 11" and the "vibrator 12" in the following descriptions concerning the collective displacement measurement process. The "phase of the vibration of the vibrator 12" is the phase of the AC electric signal sent from the signal transmitter 11 to the vibrator 12. It corresponds to the phase of the elastic wave induced in the object S at the point where the vibrator 12 is in contact with the object S. The following description initially deals with the case of $m_{max}=3$ as the simplest example and explains all steps. After that, a case with a greater value of $m_{max}$ will be described in the explanation of the modified examples.

Initially, the value of k is set to 1 (Step S1). With the vibrator 12 held in contact with an object S to be examined, an AC electric signal is sent from the signal transmitter 11 to the vibrator 12 to begin the operation of giving a vibration from the vibrator 12 to the object S (Step S2). Consequently, an elastic wave is induced in the object S. The frequency of the AC electric signal in Step S2 set at a comparatively low value of 1 MHz or lower. As a result, the elastic wave induced in the object S propagates through the object S with an approximately isotropic distribution.

Subsequently, the signal transmitter 11 transmits a pulse signal to the pulsed laser source 13 at every point in time when the vibration of the vibrator 12 is at a phase expressed as $\varphi_0+2\pi(k-1)/m_{max}$, where $\varphi_0$ is a predetermined initial value (e.g. $\varphi_0=0$). At this stage, since k=1, the phase of the vibration of the vibrator 12 at the point of transmission of the pulse signal is $\varphi_0$. The pulsed laser source 13 repeatedly emits the illuminating light in the form of a pulsed laser beam every time it receives the pulse signal. This illuminating light is expanded by the illuminating light lens 14 and cast onto the entire examination area on the surface of the object S (Step S3).

The illuminating light is reflected on the surface of the object S and hits the beam splitter 151 in the speckle-shearing interferometer 15. A portion of this incident illuminating light is reflected by the beam splitter 151. After passing through the phase shifter 153, this portion of light is reflected by the first reflector 1521 and once more passes through the phase shifter 153. A portion of this light passes through the beam splitter 151 and falls onto the image sensor 155. Meanwhile, the remaining portion of the incident illuminating light mentioned earlier passes through the beam splitter 151. After being reflected by the second reflector 1522, a portion of this illuminating light is reflected by the beam splitter 151 and falls onto the image sensor 155. In the image sensor 155, each detector element detects the illuminating light reflected at one of a large number of points on the surface of the object S.

Figure 4A:
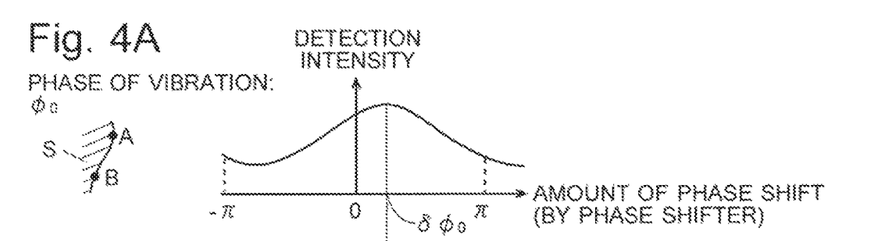
FIGS. 4A-4C are graphs for explaining the principle of the collective measurement of the displacement in the defect detection method in the present embodiment.

While the illuminating light in the form of a pulsed laser beam is repeatedly emitted, the phase shifter 153 gradually changes (shifts) the phase of the illuminating light passing through the phase shifter 153 (i.e. the illuminating light reflected at point A). This causes a gradual change in the phase difference between the illuminating light reflected at point A and the one reflected at point B. During this change, each detector element of the image sensor 155 detects the intensity of the interfering light produced by an interference of the two rays of illuminating light (Step S4). FIG. 4A graphically shows one example of the intensity of the interfering light detected by a detector element of the image sensor 155 with respect to the amount of phase shift by the phase shifter 153, which is obtained when the phase of the vibration of the vibrator 12 is $\varphi_0$. Although FIGS. 4A-4C each show a continuous curve representing the detection intensity which sinusoidally changes with the amount of phase shift, actually observed data are discrete data. Therefore, the continuous sinusoidal waveform should be reproduced from the observed data by an appropriate method, such as the least squares method. To this end, it is necessary to detect the intensity with at least three different amounts of phase shift.

Subsequently, whether or not the value of k has reached $m_{max}$ is determined in Step S5. At this stage, since the value is k=1 and has not reached $m_{max}$ (which is 3 in this example), the determination result in Step S5 is "NO". When "NO", the operation proceeds to Step S6 and the value of k is increased by 1 to k=2. (The operation which is performed when the determination result in Step S5 is "YES" will be described later.)

Next, the operation returns to Step S3. The signal transmitter 11 transmits a pulse signal to the pulsed laser source 13 at every point in time where the phase of the vibration of the vibrator 12 is $\varphi_0+2\pi(k-1)/m_{max}$ with k=2, i.e. $\varphi_0+2\pi/3 \equiv \varphi_1$. At the timing of the reception of the pulse signal, the pulsed laser source 13 repeatedly casts the illuminating light in the form of a pulsed laser beam onto the surface of the object S. While the phase of the illuminating light reflected at point A is gradually changed (shifted) to at least three values by the phase shifter 153, each detector element of the image sensor 155 detects the intensity of the interfering light produced by an interference between the illuminating light reflected at point A and passed through the phase shifter 153 (and other elements) and the illuminating light reflected at point B (Step S4).

Figure 4B:
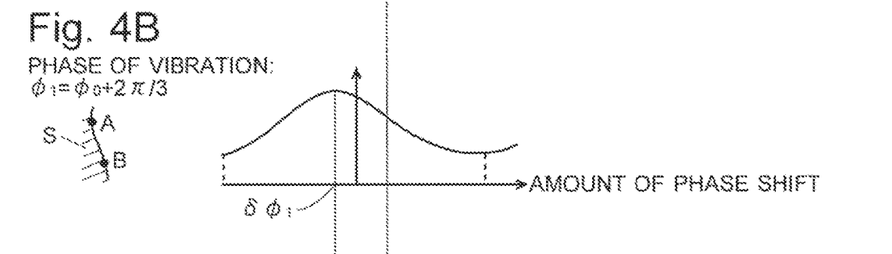

FIG. 4B graphically shows the intensity of the interfering light detected by a detector element of the image sensor 155 with respect to the amount of phase shift by the phase shifter 153, which is obtained when the phase of the vibration of the vibrator 12 is $\varphi_1$. A comparison of FIG. 4B with FIG. 4A demonstrates that the peak position of the intensity of the interfering light in FIG. 4B is displaced from the peak position in FIG. 4A by $\delta\varphi_1-\delta\varphi_0$. This displacement indicates that the phase difference between the light from point A and the light from point B has changed due to the change in the phase of the vibration of the vibrator 12 in the detecting process. This change in the phase difference of the light reflects a change in the relative displacement of points A and B in the off-plane direction.

After the operation in Step S4 with k=2 has been completed, $m_{max}$ (=3) is not reached yet in Step S5, and the determination result is "NO". Accordingly, the value of k is increased by 1 to k=3 in Step S6. Subsequently, the operation returns to Step S3. At every point in time where the phase of the vibration of the vibrator 12 is $\varphi_0+2\pi(k-1)/m_{max}$ with k=3, i.e. $\varphi_0+4\pi/3 \equiv \varphi_2$, the pulsed laser source 13 repeatedly casts the illuminating light in the form of a pulsed laser beam onto the surface of the object S, and each detector element of the image sensor 155 detects the intensity of the interfering light (Step S4). Thus, as shown in FIG. 4C, the relationship between the amount of phase shift by the phase shifter 153 and the intensity of the interfering light observed when the phase of the AC electric signal is $\varphi_2$ is obtained.

In the next step S5, since the value of k has already reached $m_{max}$=3, the determination result is "YES", and the operation proceeds to Step S7. In Step S7, the transmission of the AC electric signal from the signal transmitter 11 to the vibrator 12 is discontinued. The vibration of the vibrator 12 is thereby stopped.

Figure 4C:
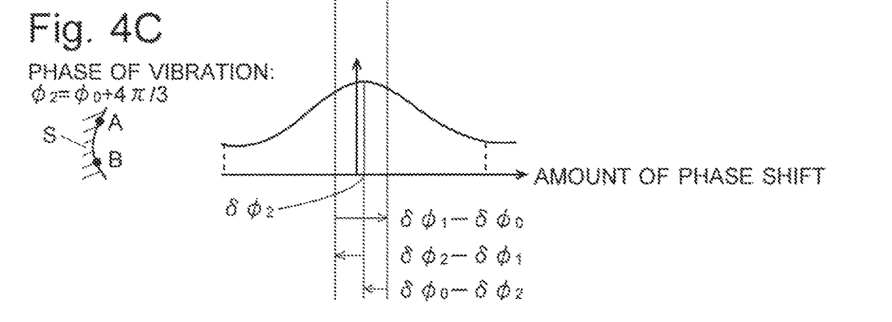

Next, for each detector element of the image sensor 155, the amount of phase shift at which the detector element yields the highest output during the operation of changing the amount of phase shift by the phase shifter 153 is determined as the output-maximizing phase-shift amount $\delta\varphi_0$, $\delta\varphi_1$ or $\delta\varphi_2$ for each of the phases of the vibration $\varphi_0$, $\varphi_1$ and $\varphi_2$, respectively (Step S8; see the graphs in FIGS. 4A-4C). Then, the difference in the output-maximizing phase-shift amount is calculated for each different combination of the phases of the vibration, i.e. $\delta\varphi_1-\delta\varphi_0$, $\delta\varphi_2-\delta\varphi_1$ and $\delta\varphi_0-\delta\varphi_2$ (Step S9). These three differences in the output-maximizing phase-shift amount represent relative displacements of the points A and B in the off-plane direction at three different phases of the vibration, i.e. at three different points in time.

(2-2) Defect Location Identification Process

Based on the three aforementioned relative displacements, the values of the following three parameters at each point in the examination area can be obtained: the amplitude of the vibration, phase of the vibration (which is the phase of the vibration at each point and is different from the phase of the vibration of the vibrator 12), and central value (DC component) of the vibration (Step S10). The amplitude and phase of the vibration change with a change of the position within the examination area. Their change is moderate at positions where no defect is present, whereas a sudden change occurs at a location where a defect is present. Thus, a defect within the examination area can be detected based on the values of the amplitude and phase of the vibration within the examination area. The detection of the defect may be simply performed based on the numerical values of the amplitude and phase of the vibration. Additionally, in the present embodiment, the location of the defect is visualized as follows: Initially, based on the values of the amplitude and/or phase of the vibration obtained in Step S10, an image is created (Step S11). For example, the difference in the amplitude of the vibration can be represented by a difference in the brightness level in the image by assigning a higher level of luminance to a pixel corresponding to a measurement point with a greater amplitude. The image created in this manner is subsequently processed by a commonly known image-processing technique to detect the surface location of defect D within the examination area (Step S12). For example, a portion where the luminance of the pixel suddenly changes with a change of the position on the image may be detected as a defect. The portion at which the luminance of the pixel suddenly changes can be identified by a visual check of the image by an operator, or it may be identified by the controller 16 based on the numerical luminance values of the pixels.

(2-3) Depth Direction Information Acquisition Process

In the depth direction information acquisition process, the vibrator-and-sensor 12 is initially placed within a limited area 21 defined so as to include the surface location, i.e. the location of the defect identified on the surface of the object S in the defect location identification process (Step S13; see FIG. 5 for this step and the subsequent steps). If there are a plurality of surface locations, the limited area 21 is defined to include one of those locations. In the present embodiment, the second elastic wave is obliquely injected to the surface location from a position displaced from the surface location within the limited area 21, using the vibrator-and-sensor 12 which is an angle probe. The limited area 21 should be defined in such a manner that the second elastic wave can be injected from a position at which a response wave originating from the defect which is present at the surface location concerned can occur. In the present embodiment, since the second elastic wave is obliquely injected, a response wave due to the reflection or the like of the second elastic wave by defect D can occur if the second elastic wave is injected from a position within a circular area centered at the surface location with a radius of $d_{max} \cdot \tan\theta$, where $\theta$ is the angle made by the travelling direction of the elastic wave in the object S and the normal to the surface of the object S, and $d_{max}$ is the largest possible value of the depth of defect D (typically, if the object S has a plate-like shape, $d_{max}$ is its thickness; see FIG. 6). Accordingly, this circular area can be defined as the limited area 21. Due to the reason which will be explained later in Step S17, it is unnecessary to keep a record of the surface position on which the vibrator-and-sensor 12 has been placed. The position at which the vibrator-and-sensor 12 is made to be in contact with the object S can be chosen by changing the position of the vibrator-and-sensor 12, which can be manually achieved by an operator watching the image or automatically under the control of the controller 16.

Next, in Step S14, the second elastic wave in a pulsed form is injected from the vibrator-and-sensor 12 into the object S. The frequency of the second elastic wave is set at a value within a range of 1-10 MHz, which is higher than the frequency of the first elastic wave. The use of the higher frequency for the second elastic wave makes the second elastic wave more directional than the first elastic wave. The second elastic wave is refracted at the surface of the object S with an angle of refraction $\theta$ determined by the material of the object S (which is the same as the aforementioned angle $\theta$), and propagates through the object S. In normal situations, the material of the object S is known beforehand, and the angle of incidence of the second elastic wave from the vibrator-and-sensor 12 to the object 12 is also known. Therefore, the angle of refraction $\theta$ is also previously known. The propagation velocity v of the second elastic wave in the object S also depends on the material of the object S, and therefore, the value of the propagation velocity v is also previously known. A portion of the second elastic wave propagating through the object S in this manner is reflected by the defect. The reflected wave enters the vibrator-and-sensor 12 and is detected as the response wave. The controller 16 stores, in the storage unit 17, the period of time from the injection of the pulse of the second elastic wave to the detection of the response wave, and the detection intensity of the response wave.

Subsequently, whether or not Step S14 has been performed a predetermined number of times is determined (Step S15). If the predetermined number of times has been reached ("YES" in Step S15), the operation proceeds to Step S17. If the predetermined number of times has not been reached ("NO" in Step S15), the position at which the vibrator-and-sensor 12 is made to be in contact with the object S is changed within the vicinity of the surface location of the defect (Step S16), and the operation of Step S14 is once more performed, followed by the determination in Step S15.

Figure 6:
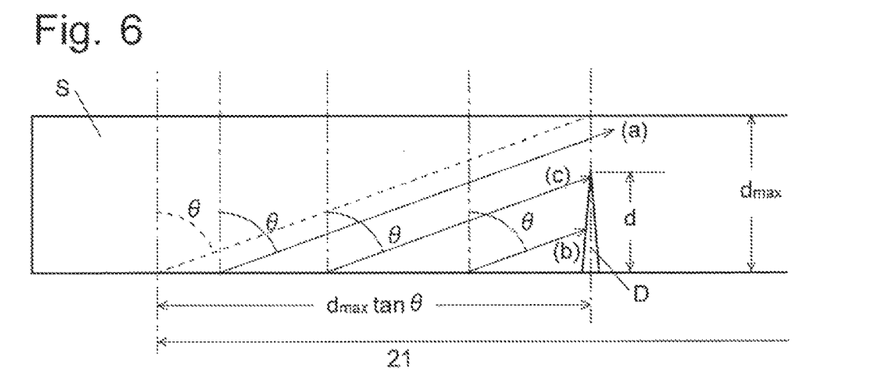
FIG. 6 is a diagram showing the relationship between the travelling direction of the second elastic wave having directionality and the location of the defect in the defect detection method in the present embodiment.

In Step S17, the controller 16 retrieves the detection intensity of the response wave obtained at each surface position and stored in the storage unit 17. The detection intensity of the response wave is low when the second elastic wave is passing through an area where defect D is not present (see arrow (a) in FIG. 6), while the intensity is high when the wave is passing through an area where defect D is present (see arrow (b) in FIG. 6). In particular, when the second elastic wave is passing through an area near the tip of defect D (see arrow (c) in FIG. 6), a reflected wave called the "tip echo" occurs, which causes the detection intensity of the response wave to be noticeably higher than when the wave is passing through any other portion of the defect. Accordingly, the controller 16 selects data which include the largest value of the detection intensity from among the data obtained at the respective surface positions retrieved from the storage unit 17. Based on the period of time t from the injection of the second elastic wave to the detection of the response wave, angle of refraction $\theta$, and propagation velocity v included in the selected data, the depth d of defect D is calculated by the following equation:

$$d = (t/2) \cdot v \cos\theta$$

By this method, no data on the surface position of the vibrator-and-sensor 12 is needed to determine depth d.

In the present example, the depth d of defect D is calculated without using data on the surface position of the vibrator-and-sensor 12. It is also possible to determine the surface position of the vibrator-and-sensor 12, and calculate the depth d of defect D based on the distance between the vibrator-and-sensor 12 and defect D on the surface of the object S at the time of the detection of the reflected wave originating from the tip echo, with reference to the angle of refraction $\theta$.

After the operations of Steps S13-S17 for one defect have been completed, those operations are similarly performed for another defect. When the operations for all defects have been completed ("YES" in Step S18), the entire series of defect-detecting operations is completed.

(2-4) Modified Examples of Collective Displacement Measurement Process

Although $m_{max}=3$ in the previous embodiment, $m_{max}$ may be given a value greater than the number expressed as $2n+1$ (where n is a natural number equal to or greater than 2) so as to allow for the detection of the nth-order component (nth-order harmonic component) of the elastic wave induced in the object S. That is to say, since $2n+1$ or more relative displacements of points A and B in the off-plane direction are obtained, the values of the following $2n+1$ parameters can be obtained: the amplitude of the fundamental harmonic, the phase of the fundamental harmonic, the amplitude of the second-order harmonic, the phase of the second-order harmonic, . . . , the amplitude of the nth-order harmonic, the phase of the nth-order harmonic, and the DC component of the elastic wave. This enables an even more accurate identification of the surface location of defect D.

In the previous embodiment, the signal transmitter-receiver 11 and the vibrator-and-sensor 12, which function as the generator of the second elastic wave and the detector of the response wave in the depth direction information acquisition process, are used as the source of induction of the first elastic wave. The signal transmitter-receiver 11 and the vibrator-and-sensor 12 may be replaced by a signal transmitter and/or vibrator which only induces the first elastic wave, and a signal transmitter-receiver and/or vibrator-and-sensor which generates the second elastic wave and detects the response wave. They may also be replaced by a signal transmitter and/or vibrator which only induces the first elastic wave, a signal transmitter and/or vibrator which only generates the second elastic wave, and a signal receiver and/or detector which only detects the response wave. In these cases, devices with fixed frequencies can be used as the signal transmitter for the first elastic wave and the signal transmitter-receiver for the second elastic wave, or as the signal transmitter for the first elastic wave, signal transmitter for the second elastic wave, and signal receiver for the response wave. It is also possible to use a signal transmitter and/or vibrator for the induction of the first elastic wave and the generation of the second elastic wave in combination with a signal receiver and/or detector which only detects the response wave, or to use a signal transmitter-receiver and/or vibrator-and-sensor for the induction of the first elastic wave and the detection of the response wave in combination with a signal transmitter and/or vibrator which only generates the second elastic wave.

In the previous embodiment, the vibrator (and detector) 12 is held in contact with the object S when in use. As in the case of using a high-power speaker, if the vibration can be transmitted to the object S in a contactless form, it is unnecessary to make the vibrator be in contact with the object S.

As for the method for collectively measuring the displacement in the back-and-forth direction of each point within the examination area in at least three mutually different phases of the elastic wave, any appropriate method other than the speckle-shearing interferometry described in the present embodiment may be used, such as the holographic interferometry, grating projection, sampling moiré method, or differential interference contrast method.

(2-5) Modified Examples of Depth Direction Information Acquisition Process

In the previous embodiment, an angle probe is used as the vibrator-and-sensor 12. Alternatively, a normal probe may also be used. In that case, the normal probe should be made to be in contact with the surface location where the defect is present. The second elastic wave is injected in the perpendicular direction to the surface of the object S, and the response wave reflected by the defect is detected with the vibrator-and-sensor 12. It is unnecessary to change the position of the vibrator-and-sensor 12 from the aforementioned surface location.

In the previous embodiment, a wave reflected by the defect is detected as the response wave. It is also possible to detect a transmitted wave, diffracted wave or other forms of wave. In the case of detecting a transmitted wave, diffracted wave or other forms of response wave, the response wave cannot be detected at the location of the source of transmission of the second elastic wave. Accordingly, in place of the vibrator-and-sensor 12, a detector which is independent of the vibrator should be placed at a different position from the vibrator. The electric signal to be detected as the vibration of the response wave is not limited to AC signals.

In the previous embodiment, the tip echo at one end of the defect is detected. If the defect is formed inside the object S and has no exposed portion on the surface of the object S, the tip echo may be detected from each of the two ends of the defect. In that case, the position in the depth direction of the invisible defect in the object S can be calculated by determining the depth of each end of the defect from the tip echo originating from each of the two ends.

REFERENCE SIGNS LIST

10 . . . Defect Detection Device
11 . . . Signal Transmitter-Receiver (Signal Transmitter)
12 . . . Vibrator-and-Sensor (Transducer)
121 . . . Vibrating Part
122 . . . Contact Part
1221 . . . Contact Surface
13 . . . Pulsed Laser Source
14 . . . Illuminating Light Lens
15 . . . Speckle-Shearing Interferometer
151 . . . Beam Splitter
1521 . . . First Reflector
1522 . . . Second Reflector
153 . . . Phase Shifter
154 . . . Condensing Lens
155 . . . Image Sensor
16 . . . Controller
17 . . . Storage Unit
21 . . . Limited Area
D . . . Defect
S . . . Object to Be Examined

The invention claimed is:

1. A defect detection method, comprising:
a) a collective displacement measurement process including: performing stroboscopic illumination on an entire surface of an object to be examined within an examination area of the object while inducing a first elastic wave across the entire examination area on the object; and controlling a phase of the elastic wave and a timing of the stroboscopic illumination to collectively measure a displacement in a back-and-forth direction of each point within the examination area in at least three mutually different phases of the elastic wave;
b) a defect location identification process including: identifying a location of a defect on a surface of the examination area, based on the displacement in the back-and-forth direction of each point within the examination area in the at least three different phases; and
c) a depth direction information acquisition process including: injecting a second elastic wave into a region inside of the object at the location from a limited area on the surface including the location of the defect on the surface; and determining a location and/or size in the depth direction of the defect, based on a response wave of the second elastic wave.

2. The defect detection method according to claim 1, wherein the second elastic wave has a higher frequency than a frequency of the first elastic wave.

3. The defect detection method according to claim 1, wherein two or three of operations of inducing the first elastic wave, injecting the second elastic wave and detecting the response wave are performed with a common transducer.

4. The defect detection method according to claim 2, wherein two or three of operations of inducing the first elastic wave, injecting the second elastic wave and detecting the response wave are performed with a common transducer.

5. The defect detection method according to claim 1, wherein both induction of the first elastic wave and injection of the second elastic wave are performed with a common oscillation circuit.

6. The defect detection method according to claim 2, wherein both induction of the first elastic wave and injection of the second elastic wave are performed with a common oscillation circuit.

7. The defect detection method according to claim 3, wherein both induction of the first elastic wave and injection of the second elastic wave are performed with a common oscillation circuit.

8. The defect detection method according to claim 4, wherein both induction of the first elastic wave and injection of the second elastic wave are performed with a common oscillation circuit.

9. The defect detection method according to claim 1, wherein the displacement in the back-and-forth direction of each point within the examination area in at least three phases is collectively measured by speckle-shearing interferometry.

10. The defect detection method according to claim 2, wherein the displacement in the back-and-forth direction of each point within the examination area in at least three phases is collectively measured by speckle-shearing interferometry.

11. The defect detection method according to claim 3, wherein the displacement in the back-and-forth direction of each point within the examination area in at least three phases is collectively measured by speckle-shearing interferometry.

12. The defect detection method according to claim 4, wherein the displacement in the back-and-forth direction of each point within the examination area in at least three phases is collectively measured by speckle-shearing interferometry.

13. The defect detection method according to claim 5, wherein the displacement in the back-and-forth direction of each point within the examination area in at least three phases is collectively measured by speckle-shearing interferometry.

14. The defect detection method according to claim 6, wherein the displacement in the back-and-forth direction of each point within the examination area in at least three phases is collectively measured by speckle-shearing interferometry.

15. The defect detection method according to claim 7, wherein the displacement in the back-and-forth direction of each point within the examination area in at least three phases is collectively measured by speckle-shearing interferometry.

16. The defect detection method according to claim 8, wherein the displacement in the back-and-forth direction of each point within the examination area in at least three phases is collectively measured by speckle-shearing interferometry.

17. A defect detection device, comprising:
a) a first elastic wave inducer for inducing a first elastic wave in an object to be examined;
b) an illuminator for performing stroboscopic illumination on an examination area on a surface of the object to be examined;
c) a displacement measurement section for collectively measuring a displacement in a back-and-forth direction of each point within the examination area in at least three mutually different phases of the first elastic wave;
d) a second elastic wave injector, for injecting a second elastic wave into the inside of the object to be examined;
e) a response wave detector for detecting a response wave of the second elastic wave; and
f) a depth direction information acquirer for determining a location and/or size in a depth direction of the defect, based on the response wave.

\* \* \* \* \*